(12) United States Patent
Valencia et al.

(10) Patent No.: US 8,608,790 B2
(45) Date of Patent: Dec. 17, 2013

(54) BIFURCATION CATHETER AND METHOD

(75) Inventors: Hans Valencia, San Jose, CA (US); Andrzej Malewicz, Minneapolis, MN (US); Adam Jennings, Buffalo, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1372 days.

(21) Appl. No.: 11/544,513

(22) Filed: Oct. 6, 2006

(65) Prior Publication Data

US 2008/0086191 A1    Apr. 10, 2008

(51) Int. Cl.
*A61F 2/06* (2013.01)

(52) U.S. Cl.
USPC .......................................... 623/1.11; 623/1.35

(58) Field of Classification Search
USPC ........... 623/1.11, 1.35, 1.27, 1.28, 1.29, 1.12; 604/53, 103, 103.01–103.09, 103.14, 604/563, 284; 606/96, 101, 284, 103, 264, 606/108, 194, 195, 198
See application file for complete search history.

(56) References Cited

U.S. PATENT DOCUMENTS

| | | | |
|---|---|---|---|
| 5,108,415 A * | 4/1992 | Pinchuk et al. | 606/194 |
| 6,129,738 A * | 10/2000 | Lashinski et al. | 606/194 |
| 6,210,429 B1 | 4/2001 | Vardi et al. | |
| 6,325,826 B1 | 12/2001 | Vardi et al. | |
| 6,579,312 B2 * | 6/2003 | Wilson et al. | 623/1.35 |
| 6,682,556 B1 * | 1/2004 | Ischinger | 623/1.35 |
| 6,692,483 B2 | 2/2004 | Vardi et al. | |
| 6,706,062 B2 | 3/2004 | Vardi et al. | |
| 6,709,440 B2 * | 3/2004 | Callol et al. | 606/108 |
| 7,220,275 B2 | 5/2007 | Davidson et al. | |
| 7,344,557 B2 * | 3/2008 | Yadin | 623/1.11 |
| 2001/0004706 A1 * | 6/2001 | Hojeibane | 623/1.11 |
| 2001/0037138 A1 | 11/2001 | Wilson et al. | |
| 2003/0125761 A1 * | 7/2003 | Meens et al. | 606/192 |
| 2003/0181923 A1 | 9/2003 | Vardi | |
| 2004/0122465 A1 * | 6/2004 | McMurtry et al. | 606/194 |
| 2004/0138737 A1 | 7/2004 | Davidson et al. | |
| 2004/0176837 A1 | 9/2004 | Atladottir et al. | |
| 2005/0015108 A1 | 1/2005 | Williams et al. | |
| 2005/0060027 A1 * | 3/2005 | Khenansho et al. | 623/1.35 |
| 2005/0102019 A1 * | 5/2005 | Yadin | 623/1.11 |

(Continued)

FOREIGN PATENT DOCUMENTS

| | | |
|---|---|---|
| EP | 0 965 311 A2 | 12/1999 |
| WO | WO 2004/093968 A1 | 11/2004 |
| WO | WO 2005/084130 A2 | 9/2005 |

*Primary Examiner* — Jonathan Hollm
(74) *Attorney, Agent, or Firm* — Seager, Tufte & Wickhem, LLC (57) ABSTRACT

A catheter assembly for treatment of a vessel bifurcation. The catheter assembly is adapted for use with a single guidewire, wherein the guidewire is used to both position the catheter assembly within a main vessel of the vessel bifurcated and then be advanced into a branch vessel of the vessel bifurcated. A guidewire lumen of the catheter assembly is defined by a portion of a catheter shaft of the catheter assembly and a portion of a side catheter branch of the catheter assembly. The side catheter branch extends from a distal end of the catheter shaft at a proximal location and is connected at a distal location to a main catheter branch. After the catheter assembly has been advanced over the guidewire to a position within the main vessel at the vessel bifurcation, the guidewire is retracted, a portion of the side catheter branch is advanced into the branch vessel, and the guidewire is advanced into the branch vessel.

14 Claims, 5 Drawing Sheets

(56) References Cited

U.S. PATENT DOCUMENTS

| | | | |
|---|---|---|---|
| 2005/0209677 A1* | 9/2005 | Shaked | 623/1.11 |
| 2007/0016241 A1* | 1/2007 | von Oepen et al. | 606/192 |
| 2007/0203562 A1* | 8/2007 | Malewicz et al. | 623/1.11 |
| 2008/0051869 A1* | 2/2008 | Yribarren | 623/1.11 |
| 2008/0109060 A1* | 5/2008 | Yadin | 623/1.11 |
| 2010/0087909 A1* | 4/2010 | Williams et al. | 623/1.11 |

* cited by examiner

BIFURCATION CATHETER AND METHOD

TECHNICAL FIELD

This disclosure relates to bifurcation treatment systems and related methods of treating a bifurcation. Preferred arrangements also relate to catheter configurations adapted for positioning the bifurcation treatment system at a bifurcation treatment site.

BACKGROUND

Catheters are used with stents and balloon inflatable structures to treat strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular body organ for treating conditions such as, for example, occlusions, stenoses, aneurysms, dissection, or weakened, diseased, or abnormally dilated vessel or vessel wall, by expanding the vessel or by reinforcing the vessel wall. Stents can improve angioplasty results by preventing elastic recoil and remodeling of the vessel wall and treating dissections in blood vessel walls caused by balloon angioplasty of coronary arteries.

While conventional stent technology is relatively well developed, stent technologies related to treatment of the region of a vessel bifurcation are still being developed.

SUMMARY OF THE DISCLOSURE

The present disclosure relates generally to catheter assemblies for treatment of bifurcated lumens in a patient, such as vessel bifurcations. In one example, the catheter assembly is adapted for use with a single guidewire, wherein the guidewire is used to both position the catheter assembly within a main vessel of the vessel bifurcation and then be advanced into a branch vessel of the vessel bifurcation. A guidewire lumen of the catheter assembly is defined by portions of a catheter shaft, a main catheter branch of the catheter assembly, and a side catheter branch of the catheter assembly. The side catheter branch includes a side catheter branch segment and a distal receiver that are axially spaced from each other. After the catheter assembly has been advanced over the guidewire to a position within the main vessel at the vessel bifurcation, the guidewire is retracted distally in the guidewire lumen, the side catheter branch segment is advanced into the branch vessel, and the guidewire is advanced through the side catheter branch segment into the branch vessel.

There is no requirement that an arrangement include all features characterized herein to obtain some advantage according to this disclosure.

DETAILED DESCRIPTION

I. General Background

This disclosure relates to bifurcation treatment systems and related methods of treating bifurcations in a patient's body. The term bifurcation means a division location from one unit into two or more units. Generally, two types of bifurcations of a body organ include 1) a main tubular member defining a main lumen and a branch tubular member defining a branch lumen that extends or branches off from the main tubular member, wherein the main and branch lumens are in fluid communication with each other, and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel). The term conduit means a channel (e.g., a pipe or tube) through which something such as a fluid is conveyed. The terms lumen and conduit are used interchangeable throughout this document.

An example bifurcation is a vessel bifurcation that includes a continuous main vessel and a branch vessel, wherein the vessels define a main lumen and a branch lumen, respectively that are in fluid communication with each other. A vessel bifurcation can alternatively include a parent vessel that divides into first and second branch vessels, wherein the vessels define a parent lumen and first and second branch lumens, respectively, which lumens are all in fluid communication with each other.

The example bifurcation treatment systems disclosed herein include a catheter shaft defining a catheter shaft conduit, a main catheter branch defining a main catheter branch conduit, and a side catheter branch including a distal guidewire receiver and a side catheter branch segment that are spaced axially from each other. The side catheter branch segment defines a side branch guidewire conduit. Portions of the catheter shaft conduit, the main catheter branch conduit, and the side branch guidewire conduit define a first guidewire lumen through which a guidewire can pass. Each of the catheter shaft, main catheter branch, and side catheter branch can define multiple lumens or conduits, wherein each lumen or conduit has a specific structure and function (e.g., sized to receive a guidewire or configured to pass inflation fluid). When multiple lumen are present in a single catheter branch, the lumens can extend co-lineally (e.g., side-by-side) or coaxially (one within the other).

The bifurcation treatment systems disclosed herein can further include a stent. The bifurcation treatment systems can be adapted to position the stent at a bifurcation treatment site. A primary aspect of the examples disclosed herein is the use of a single guidewire to both position the catheter assembly within a main vessel across the vessel bifurcation, and after proximal retraction of the guidewire advancing the guidewire into a branch vessel of the vessel bifurcation.

A single guidewire system can have advantages over a two guidewire bifurcation treatment system. One advantage of a single guidewire system is elimination of relative twist between guidewires that is common in two guidewire bifurcation treatment systems. Relative twist between guidewires can inhibit advancement of a catheter assembly over the guidewires to a bifurcation treatment sight. Relative twist can also adversely affect radial alignment of features of the bifurcation treatment systems relative to the vessel bifurcation.

While the disclosed embodiments are directed primarily to bifurcation treatment systems that can be used with a single guidewire, the same or similar systems can also be used with two guidewires. The use of two guidewires may affect some of the advantages of a single guidewire system described above, but can provide other advantages over a single guidewire system. For example, the capability of using two guidewire can make it possible to maintain a guidewire in the main branch of the vessel bifurcation before, during, and after treatment of the vessel bifurcation using the catheter assemblies described herein.

A variety of stents can be used with the bifurcation treatment systems disclosed herein. Examples of such stents can be found in, for example, in U.S. Pat. Nos. 6,210,429, 6,325,826 and 6,706,062 to Vardi et al., co-pending U.S. patent application Ser. No. 10/644,550, filed on Aug. 21, 2003, and titled STENT WITH A PROTRUDING BRANCH PORTION FOR BIFURCATED VESSELS, and U.S. Published Patent Application No. 2004/0176837 titled SELF-EXPANDING STENT AND CATHETER ASSEMBLY AND METHOD FOR TREATING BIFURCATIONS, the entire contents of which are incorporated herein by reference. In general, the aforementioned stents include a lateral branch opening located on a sidewall of the stent at a location between distal and proximal open ends of the stent. The lateral branch opening defines a path between an inner lumen of the stent and an area outside of the stent. The stent lateral branch opening is distinct from the cell openings defined between strut structures from which the stent sidewall is constructed. In some stents, the lateral branch opening can be surrounded by expandable structure. The expandable structure can be configured to extend radially into the branch lumen of the bifurcation upon expansion of, for example, an inflatable portion of the bifurcation treatment system. Typically, the stent is expanded after being positioned in the main vessel of the vessel bifurcation with the lateral branch opening aligned with an opening into the branch vessel. Alignment of the lateral branch opening with the opening into the branch vessel includes requires radial and axial alignment. The stent, including the expandable structure surrounding the lateral branch opening, can be expanded with a single expansion or multiple expansions using one or more inflatable balloons.

II. The Example Illustrated in FIGS. 1-3

Figure 1:
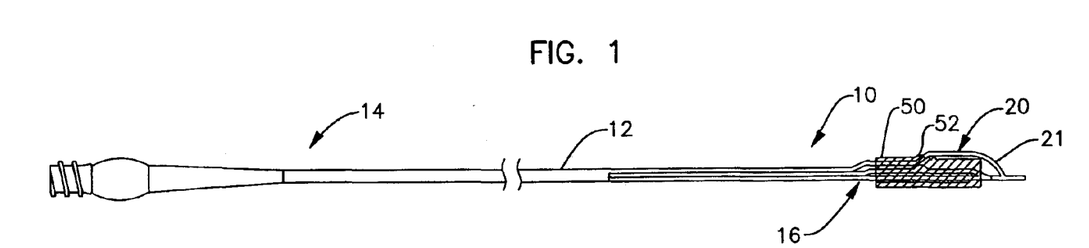
FIG. 1 is a schematic side view of an example bifurcation treatment system constructed according to principles of this disclosure.
Figures 2, 2A, 3:
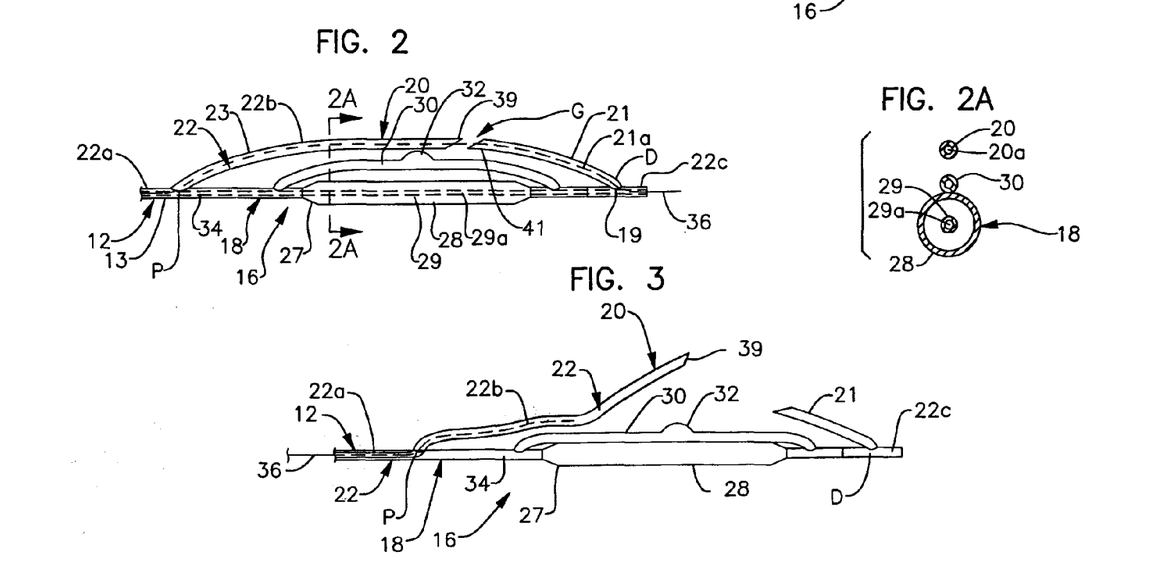
FIG. 2 is a schematic side view of distal end features of the bifurcation treatment system shown in FIG. 1, the system including a guidewire extending through a side catheter branch.
FIG. 2A is a schematic cross sectional view of the bifurcation treatment system shown in FIG. 2 taken along indicators 2A-2A.
FIG. 3 is a schematic side view of the distal end features shown in FIG. 2 with the guidewire retracted from the side catheter branch and a portion of the side catheter branch extending laterally from the main catheter branch.

An illustrative view of an example bifurcation treatment system 10 constructed in accordance with the present disclosure is shown in FIG. 1. Bifurcation treatment system 10 includes a main catheter shaft 12 extending from a proximal end portion 14 to a distal end portion 16. As best seen in FIG. 2, distal end portion 16 includes a main catheter branch 18 and a side catheter branch 20. The main catheter shaft 12 defines a shaft lumen 13. The main catheter branch 18 includes a guidewire shaft 29 that defines a main lumen 29a therein that is sized to pass over a guidewire (see FIG. 2A). The side catheter branch 20 defines a side lumen 20a also sized to pass over a guidewire (see FIG. 2A). FIG. 2A illustrates in cross-sectional view the guidewire shaft 29, main lumen 29a, side catheter branch 20, and side lumen 20a. The main lumen 29a is also referred to as a main catheter branch conduit. The side lumen 20a is also referred to as a side branch guidewire conduit.

The side catheter branch 20 includes distal and proximal segments 21, 23. The proximal segment 23 is also referred to as a side catheter branch segment. The distal segment 21 is also referred to as a distal guidewire receiver or side catheter branch extension. The distal and proximal segments 21, 23 are spaced axially from each other to define a spacing or gap G. The term gap means a separation in the structure along a length of the object defined by a separation or spacing between two portions of the object. The spacing or gap G defines a portion of the side catheter branch 20 that is material-free and materialless, or structure-free and structureless along a length of the side catheter branch 20. That is, the side catheter branch 20 does not include material or structure in the spacing or gap G between a distal end of the segment 23 and a proximal end of the segment 21.

The gap G shown in FIGS. 1-3 permits relative movement of the distal and proximal segments 21, 23 when there is no guidewire (e.g., guidewire 36) extending across the gap between segments 21, 23. A distal end 39 of the proximal segment 23 is also referred to as a free end or a distal tip of the proximal segment 23. The proximal segment 23 is adapted to move relative to the main catheter branch 18 and distal segment 21 as described in further detail below.

The gap G has a sufficient size to permit relative movement of the distal and proximal segments 21, 23. A size of the gap G is typically measured when the bifurcation treatment system 10 is assembled and ready for insertion into a patient, such as the assembled configuration shown in FIGS. 1 and 4. The size of gap G, as measured between a proximal most portion of distal segment 21 and a distal most portion of proximal segment 23 can be defined as a percentage or multiple of a dimension of one of the distal and proximal segments 21, 23. For example, the gap G can be at least about ¼ to about 3 times the greatest outer dimension of the distal segment 21. The greatest outer dimension of the distal segment 21 can be, for example, an outer diameter if the distal segment 21 has a circular cross-section.

The gap G can also be sized and configured such that the distal and proximal segments 21, 23 are in engagement with each other prior to extension of the proximal segment 23 into an extended position extending radially away from the main catheter branch 18. Engagement of the distal and proximal segments 21, 23 can provide a smooth transition between the distal and proximal segments 21, 23 that reduces the likelihood of undesired snagging or other engagement of the distal tip 39 of the proximal segment 23 during advancement of the system 10 to a bifurcation treatment site. The ends of distal and proximal segments 21, 23 across which the gap G is measured can have tapers formed therein as shown in FIG. 2. Opposing tapered structures on these free ends of the segments 21, 23 can promote relative movement of the segments 21, 23 without interference with each other, in particular if the gap G is relatively small.

The side catheter branch 20 in the area of gap G can be covered with a coating or sealing-type agent or structure that creates a smooth transition area between the distal and proximal segments 21, 23. Such a coating or sealing-type agent can temporarily fill at least a portion of the gap G for purposes of advancing the system 10 to a bifurcation treatment site without the free ends of the distal and proximal segments 21, 23 inhibiting movement of the system 10 within a vessel. The coating or sealing-type agent can be broken or removed from the area of gap G at the time of extending the proximal segment 23 into a branch vessel of the vessel bifurcation.

Typically, the side catheter branch 20 does not include an inflatable portion such as an inflatable balloon. The side catheter branch 20 can be considered balloonless or balloon-free in some arrangements. In other arrangements, at least one of the distal and proximal segments 21, 23 includes an inflatable member (not shown). An inflatable member positioned on the proximal segment 23 could be used to expand portions of a stent, such as expandable structure surrounding a lateral branch opening 52 in stent 50, described below.

The main catheter branch 18 includes first and second branch portions 27, 30. First branch portion 27 includes an elongate inflatable portion 28. Second branch portion 30 includes a second inflatable portion 32 (also referred to as an auxiliary inflatable portion). Second branch portion 30 defines an inflation lumen that is in fluid communication at a proximal end thereof with an inflation lumen defined by the first branch portion 27 at a location proximal of the inflatable portion 28. The second branch portion 30 extends adjacent to inflatable portion 28. A distal end of second branch portion 30 is connected to first branch portion 27 at a location distal of the inflatable portion 28. Alternatively, the distal end of branch portion 30 can be removably attached to the first branch portion 27.

In the example shown, the first inflatable portion 28 is generally cylindrical. Second inflatable portion 32 can have a shape and size adapted to extend into a branch vessel of the vessel bifurcation. In alternative applications, the branch 30 can be eliminated. The inflatable portion 32 can be integrated into the side catheter branch 20. The inflatable portion 32 can also be integrated into the first branch portion 27 of the main catheter branch 18, as described in co-pending U.S. Published Application No. 2005/015108 titled CATHETER BALLOON SYSTEMS AND METHODS, which is incorporated herein by reference.

The inflatable portions 28, 32 can be configured as inflatable balloons structures. The inflatable portions 28, 32 and all other balloons disclosed herein can be made of any suitable balloon material including compliant and non-compliant materials and combinations thereof. Some example materials include thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and polyetherpolyamide copolymers. One suitable material is Surlyn®, a copolymer polyolefin material (DuPont de Nemours, Wilmington, Del.). Still further suitable materials include thermoplastic polymers and thermoset polymeric materials, poly(ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L21011F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356, which is incorporated herein by reference.

Typically, the second inflatable portion 32 is longitudinally positioned at a midpoint of the first inflatable portion 28 measured from distal and proximal ends of the second inflatable portion 32. Alternative applications can include a second inflatable portion 32 that is positioned at any longitudinal location along a length of the first inflatable portion 28.

In the example shown in FIGS. 1-3, the branch portions 27, 30 have a common inflation lumen 34. The term inflation lumen means a cavity of a tubular structure through which fluid passes for inflation of an inflatable member. Alternatively, the branch portions 27, 30 have fluidly separated inflation lumens. Inflation lumen 34 can extend from the proximal end portion 14 of the bifurcation treatment system that remains outside of the patient to the branch portions 27, 30. Inflation lumen 34 can simultaneously be in fluid communication with the interiors of first inflatable portion 28 and second inflatable portion 32. Inflation lumen 34 is used to supply pressurized inflation fluid to inflatable portions 28, 32. Inflation lumen 34 is also used to drain inflation fluid from the inflatable portions 28, 32 when it is desired to deflate the balloon. First and second inflatable portions are initially deflated when directing the bifurcation treatment device to the bifurcation treatment site in a patient. In the example shown in FIGS. 1-3, the inflation lumen 34 inflates inflatable portions 28, 32 substantially simultaneously.

In some configurations, branch balloon portions 27 and 30 have separate inflation lumens. In this alternative example, inflatable portions 28 and 32 can be inflated simultaneously or sequentially. When sequential inflation is desired, an example order for inflation is to inflate the first inflatable portion 28 first, followed by inflation of the second portion 32.

The bifurcation treatment system 10 defines a guidewire lumen 22 (also referred to as a guidewire path or guidewire conduit) that is adapted for passing the bifurcation treatment system 10 over a guidewire 36. The example illustrated in FIGS. 1-3 includes a guidewire lumen 22 that is defined in part by the main catheter shaft 12, the main catheter branch 18, and the side catheter branch 20. FIGS. 2 and 3 illustrate three guidewire lumen sections 22a, 22b, 22c. In section 22a, the guidewire lumen 22 extends within the main catheter shaft 12. The guidewire lumen 22 is then diverted into the side catheter branch 20 at a proximal intersection location P. The guidewire lumen 22 extends from within the side catheter branch 20 into the main catheter branch 18 at a distal location D.

The proximal location P defines a connection location or point for a proximal end of the side catheter branch 20, a proximal end of the main catheter branch 18, and a distal end of the main catheter shaft 12. At least the side lumen 20a and shaft lumen 13 are in flow communication with each other at proximal location P. The main lumen 29a can also be in flow communication with the shaft lumen at the proximal location P. The proximal location P is typically proximal of the inflatable portions 28, 32.

The side catheter branch 20 is connected to the main catheter branch 18 at a distal intersection location D. The distal location D is distal of the inflatable portions 28, 32. The section 22b extends from the proximal location P to the distal location D. The section 22c extends through the distal end 19 of the main catheter branch 18 distally of the distal location D. The main lumen 29a and side lumen 20a are in flow communication with each other at the distal location D.

The length of the section 22b measured from location P to location D along the side catheter branch 20 is typically longer than a path from location P to location D along the main catheter branch 18. The length of side catheter branch 20 measured from location P to location D is typically longer because it extends over the inflation portion 32, whether the inflation portion 32 is part of a second branch portion 30 or is integrated into the first branch portion 30. The inflation portion 32 typically results in an increased diameter for the main catheter branch 18.

In the example shown in FIGS. 1-3, the path between locations P, D through the side catheter branch 20 is at least 5% greater than the path between locations P, D through the main catheter branch 18. In one example, the path between locations P, D through the side catheter branch 20 can be about 5% to about 25% greater than the path between locations P, D through the main catheter branch 18.

The side catheter branch 20 shown in FIGS. 1-3 includes arcuate shaped portions between locations P, D. The term arcuate shaped means a shape having a non-linear, generally arc shape like the shape of a bow. Alternatively, the main catheter branch 18 can include arcuate shaped portions between locations P, D, or both the main and side catheter branches 18, 20 can include arcuate shaped portions between locations P, D. The arcuate shape of branches 18, 20 can result in part from positioning at least portions of the main and side catheter branches 18, 20 within a stent, such as stent 50 shown in FIG. 4. The main catheter branch 18 can in other examples have a length between locations P, D that is greater than a length of side catheter branch 20 between locations P, D. In still other examples, the main catheter branch 18 can have a length between locations P, D that is substantially the same as a length of side catheter branch 20 between locations P, D. The shape of main and side catheter branches 18, 20 between locations P, D can also be substantially linear.

Typically, guidewire lumens in catheters have a singular purpose. A main guidewire lumen usually extends only through a main catheter branch of a bifurcation treatment system and remains generally coaxial with an axis of the main catheter branch and an axis of the main catheter shaft from which the main catheter branch extends. For example, FIG. 3 illustrates a main guidewire lumen 29a defined extending through the balloon 28 between the proximal and distal locations P, D. A separate side branch guidewire lumen 20a typically extends only through a side catheter branch of the bifurcation treatment system and remains generally coaxial with an axis of the side catheter branch 20. The main guidewire lumen 29a is adapted for tracking over a main guidewire used to orient the bifurcation treatment system at a desired axial location within a main vessel of the vessel bifurcation. The side branch guidewire lumen 20a is adapted for tracking over a side branch guidewire that is positioned within a branch vessel of the vessel bifurcation to orient the side catheter branch 20 within the branch lumen of the vessel bifurcation. The guidewire lumen 22 defined by sections 22a-c of FIGS. 1-3 provides functional aspects of both a main guidewire lumen for tracking over a main branch guidewire and a side branch guidewire lumen for tracking over a side branch guidewire. The guidewire lumen of FIGS. 1-3 makes possible the use of a single guidewire 36 for both axial positioning of the bifurcation treatment system 10 within a main vessel of a vessel bifurcation and positioning the side catheter branch within a branch vessel of the vessel bifurcation.

In the example depicted in FIGS. 1-3, the side catheter branch 20 does not include an inflatable balloon. Alternatively, side catheter branch 20 can include an inflatable portion, as described for example in co-pending U.S. patent application Ser. No. 10/644,550 entitled STENT WITH A PROTRUDING BRANCH PORTION FOR BIFURCATED VESSELS. Side catheter branch 20 can be distinct and fluidly separated from inflation lumen 34 that supplies inflation fluid to inflatable portions 28, 32. Alternatively, portions of the side catheter branch 20 can be in fluid communication with the inflation lumen 34 or separate inflation lumen (not shown) if the side catheter branch 20 were to include an inflatable portion.

As shown in the example of FIGS. 1-3, side catheter branch 20 extends distally and proximally of first and second branch portions 27, 30 of the main catheter branch 18. In operation, the side catheter branch 20 can extend through a lateral branch opening 52 of the stent 50 that is defined in a sidewall of the stent 50 between distal and proximal open ends of the stent 50. The lateral branch opening 52 is distinct from the plurality of cell openings defined in the stent sidewall.

In the illustrated example of FIGS. 1-3, the proximal segment 23 of side catheter branch 20 includes a free end 39. The extension 21 is connected at distal location D to the distal end 19 of main catheter branch 18. The extension 21 defines a distal guidewire receiver lumen 21a. A proximal end 41 of extension 21 is open and sized to receive the guidewire 36 into the distal guidewire receiver lumen 21a. The extension 21 can function as a retaining structure that holds the proximal segment 23 of the side catheter branch 20 in a retained position (shown in FIG. 2) when the guidewire 36 extends through the proximal segment 23 and the extension 21. When the guidewire 36 is retracted proximally beyond the gap G towards the proximal location P, the proximal segment 23 is released from the retained position. The free end 39 of the side catheter branch 20 can extend radially away from the main catheter branch 18 (shown in FIG. 3) after the proximal segment 23 is released. Further advancing the distal end of the guidewire back into the extension 21 results in the proximal segment 23 maintaining the retained position. The guidewire 36 can alternatively be advanced into the main lumen 29a after having been retracted proximal of the proximal location P.

FIG. 2 illustrates the guidewire 36 positioned within the guidewire portions 22a, 22b, 22c. When the distal end portion 16 of the bifurcation treatment system 10 is positioned at a desired location within a vessel, the guidewire is retracted beyond the gap G. After the guidewire is retracted, the proximal segment 23, including the free end 39, can extend away from the main catheter branch 18 as shown in FIG. 3. The extended side catheter branch 20 can be used to align the distal end portion 16 relative to a branch lumen of a bifurcation as discussed below with reference to FIGS. 4-6. For example, the proximal segment 23 can protrude into a branch vessel of a vessel bifurcation to align the system 10 relative to the branch vessel. The guidewire 36 can be directed through the extended side catheter branch 20 into the branch vessel.

The proximal segment 23 can be configured to actively move away from the main catheter branch 18. This active movement can occur using a variety of methods and practices such as those described below with reference to FIGS. 8A-12B. The active movement of proximal segment 23 can result from, for example, the use of stored potential energy, a thermal shape memory material, or a current-induced pseudo-elastic material.

III. The Example Illustrated in FIGS. 4-6

Figure 4:
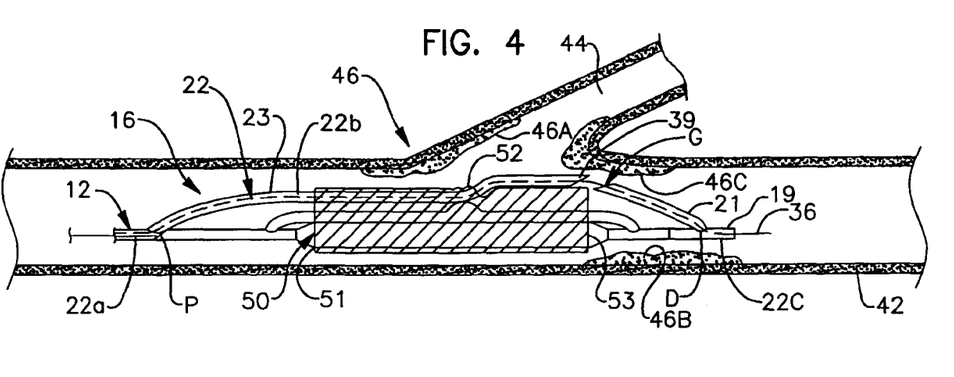
FIG. 4 is a schematic side view of the distal end features of the bifurcation treatment system shown in FIG. 1 positioned adjacent a vessel bifurcation, the system including a guidewire extending through the side catheter branch and a stent having a lateral branch opening.
Figure 5:
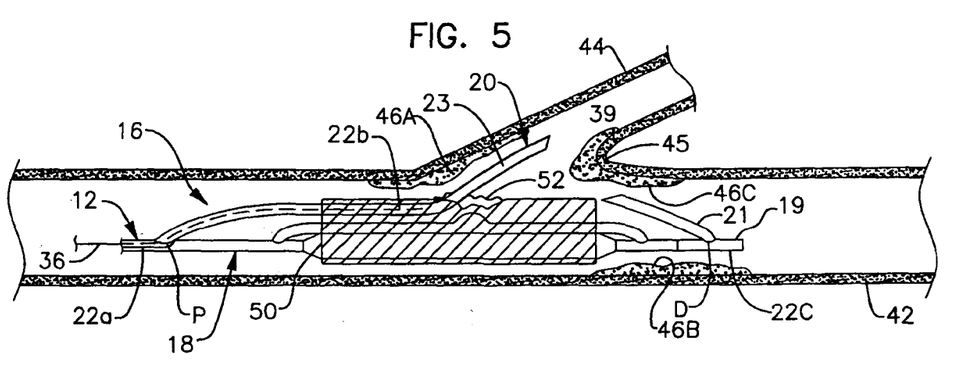
FIG. 5 is a schematic side view of the features shown in FIG. 4 with the guidewire retracted from the side catheter branch and a portion of the side catheter branch extending laterally through the lateral branch opening of the stent.
Figure 6:
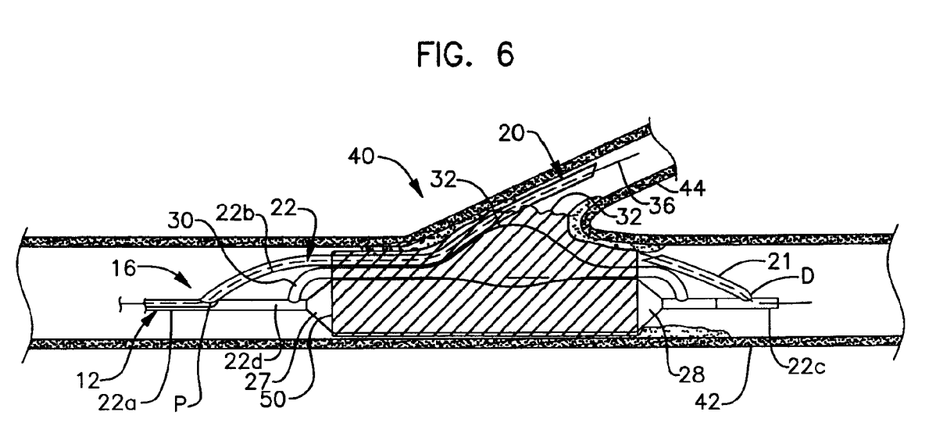
FIG. 6 is a schematic side view of the features shown in FIG. 4 with the guidewire reinserted through the side catheter branch into the side branch vessel and the balloon features of the bifurcation treatment system expanded.

With reference to FIGS. 4-6, an exemplary manner of practicing aspects of the disclosed system and methods will now be discussed. Referring to FIGS. 4-6, the delivery system 10 is shown in relation to a vessel bifurcation 40. The vessel bifurcation 40 includes a plurality of plaque obstructions 46A-C positioned on portions of a main vessel 42 and a branch vessel 44 of the bifurcation 40. The plaque obstructions 46A and 46C are positioned at an ostium (or opening) into the branch vessel 44.

FIG. 4 shows the distal end portion 16 of the bifurcation treatment system 10 positioned within the main vessel 42 adjacent to the branch vessel 44. A stent 50 is positioned around portions of the main and side catheter branches 18, 20. The stent lateral branch opening 52 is aligned facing the ostium of branch vessel 44. The guidewire 36 extends through a guidewire lumen 22. The guidewire lumen 22 includes a first section 22a in a portion of the main catheter shaft 12 proximal of a proximal intersection location P with the side catheter branch 20. A second portion 22b of the guidewire lumen 22 extends through the side catheter branch 20 between the proximal location P and a distal intersection location D where the distal end of the side catheter branch 20 intersects with the main catheter branch 18. A third section 22c of the guidewire lumen 22 extends through a distal end 19 of the main catheter branch 18 distally of the side catheter branch 20. The guidewire lumen 22 extends through the side branch extension 21 along second section 22b.

Figure 7:
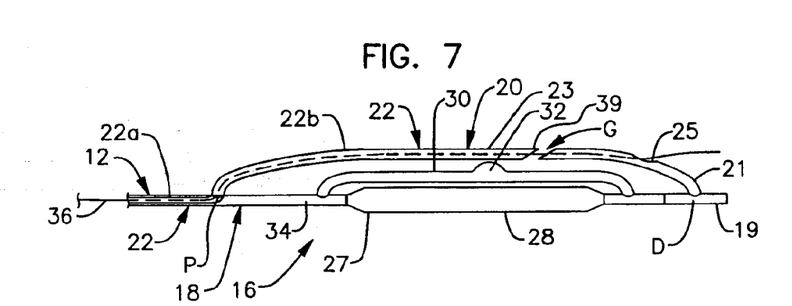
FIG. 7 is a schematic side view of the distal end features of another example bifurcation treatment system, wherein the guidewire extends through a distal end of the side catheter branch.
Figure 8A:
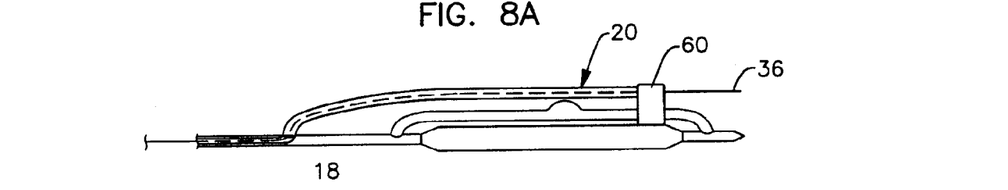
FIG. 8A is a schematic side view illustrating distal end features of another example bifurcation treatment system, wherein the side catheter branch is secured to the main catheter branch with a fastener device.
Figure 8B:
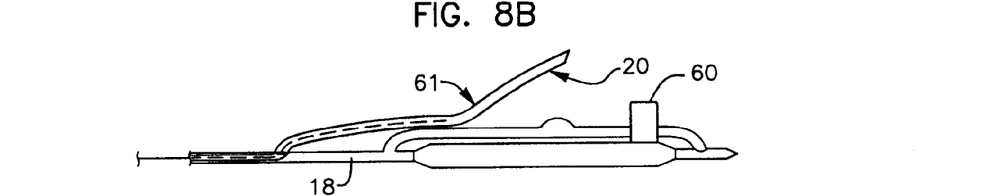
FIG. 8B is a schematic side view of the distal end features shown in FIG. 8A with the side branch lumen released from the fastener device and extending laterally from the main catheter branch.

Positioning the guidewire 36 within the extension 21 and segment 23 holds the free end 39 of segment 23 in a retained position. FIG. 4 illustrates the distal end of the guidewire 36 passing through the third section 22c and out of the distal tip of the main catheter branch 18. Other examples, such as the example illustrated in FIG. 7, are configured to permit the guidewire to exit the side catheter branch 20 along the length of second section 22b. In the example of FIG. 7, the guidewire exits the side branch extension 21 at an opening 25 that is proximal of the distal intersection location D and distal of the gap G. The opening 25 is defined in a sidewall of the extension 21 and is in flow communication with a lumen defined within the extension 21 that is sized to receive the guidewire 36.

In the illustrated example, the lateral branch opening 52 is larger than the cell opening defined in the stent sidewall between proximal and distal ends 51, 53 of the stent 50. The cell openings of the stent 50 are defined by the continuous strut structure of the stent 50. The cell openings typically enlarge upon expansion of the stent. In other examples, the lateral branch opening 52 has the same or smaller size than the stent cell openings. In one example, the lateral branch opening 52 is defined by a band of continuous material that defines a perimeter of the lateral branch opening 52. This continuous band of material preferably includes discontinuities over its length so that the area of the lateral branch opening 52 expands together with the expansion of the stent 50. In some configurations, the continuous band includes protrusions that project inwardly from a peripheral edge of the lateral branch opening 52 in a direction axially relative to the opening 52. These protrusions (also referenced as expandable portions) are initially oriented parallel with a longitudinal dimension (e.g., length along a longitudinal axis) of the stent. These protrusions can expand at least partially radially outward from a sidewall of the stent 50 upon inflation of, for example, the auxiliary expandable portion 32.

In operation, the guidewire 36 of the illustrated example is first positioned within the main vessel 42 with a distal end of the guidewire extending distally to the vessel bifurcation 40 at a position distally beyond the ostium of the branch vessel 44. A proximal end of the guidewire (not shown) is fed into the distal tip 19 of the main catheter branch 18. The guidewire is fed through the sections 22a, 22b, 22c of the guidewire lumen. The bifurcation treatment system 10 is guided over the guidewire 36 into an axial position adjacent to the vessel bifurcation 40 (see FIG. 4). The main catheter branch 18 can be specially structured with additional stiffness at least between locations P, D (e.g., using increased stiffness in guidewire lumen 29) to ensure proper tracking of the system 10 over the guidewire 36 with the guidewire in sections 22a, 22b, 22c. The example bifurcation treatment systems disclosed herein can be used with over-the-wire or rapid exchange systems. A rapid exchange system is described in at least U.S. Published Appl. No. 2003/0181923 to Vardi et al., the entire contents of which is incorporated herein by reference.

The stent 50 is usually releaseably secured to main catheter branch 18 and side catheter branch 20 using, for example, a crimping technique. Axial and radial alignment of features of the bifurcation delivery system 10 relative to each other and to the vessel bifurcation can be achieved using markers and marker materials, such as those markers and marker materials described in U.S. Pat. No. 6,692,483 to Vardi, et al., and co-pending U.S. provisional patent application Ser. No. 60/776,149, filed on Feb. 22, 2006, and titled MARKER ARRANGEMENT FOR BIFURCATION CATHETER, which patent matters are incorporated herein by reference. For example, at least two axially spaced apart markers can be positioned on each of the main catheter branch 18 and side catheter branch 20. Relative positioning of the four markers can provide information about relative twist between the main and side catheter branches 18, 20. Information about relative radial position can be used in axial and radial alignment of the bifurcation delivery system 10 relative to the vessel bifurcation 40.

Referring now to FIG. 5, guidewire 36 is retracted proximally from the side branch extension 21 and the gap G. Typically, the guidewire 36 is retracted to a position proximal of at least the stent lateral branch opening 52. With the guidewire 36 retracted, the free end 39 of the proximal portion 23 can move away from the main catheter branch 18 into an extended position. The bifurcation treatment system 10 is then adjusted axially and radially to position the free end 39 within the ostium of the branch vessel 44. The system 10 can be advanced distally to further advance the proximal portion 23 into the branch vessel 44. Additional radial and axial adjustment of the system 10 relative to the bifurcation 40 can be done until at least one of the lateral branch opening 52 and auxiliary inflatable portion 32 are aligned with the ostium of branch vessel 44.

The proximal portion 23 of the side catheter branch 20, when extended into the branch vessel 44, can also be used to direct the guidewire 36 into the branch vessel 44. The side catheter branch 20, when extended into the branch vessel 44, can also be used to orient other guidewires besides guidewire 36 and alternative treatment devices into the vessel 44.

After the free end 39 of the side catheter branch 20 is positioned within the branch vessel 44, the distal end portion 16 can be advanced distally until resistance to distal movement occurs resulting from engagement of the side catheter branch 20 with a carina 45 of the vessel bifurcation 40. When this resistance occurs, a certain amount of radial and axial alignment of the stent lateral branch opening 52 can be assumed. In some cases, the physician can retract proximally the operating system 10 a predetermined distance after the resistance in the axial direction is felt in order to better axially align the stent opening 52 with the branch vessel ostium.

When the free end 39 of the proximal portion 23 and the guidewire 36 are positioned within the branch vessel 44, pressurized fluid is supplied to first and second branches 27, 30 to inflate the first and second inflatable portions 28, 32. Inflating the inflatable portion 28 causes expansion of the stent 50 against internal walls of the main vessel 50 (see FIG. 6). Inflating the inflatable portion 30 expands the stent lateral branch opening 52 and the expandable structure of the stent 50 surrounding the opening 52 as described further below. A similar expanding function can be provided with alternative catheter designs such as, for example, a main catheter branch that includes a second inflatable portion integrated into the first inflatable portion as a "blister" or "bulge" type balloon structure.

Expanding the opening 52 can provide a larger path through the interior of stent 50 into branch vessel 44 for passage of addition treatment and alignment devices. Inflating the inflatable portion 30 can also extend expandable structure that surrounds the opening 52. Examples of expandable structure surrounding the lateral branch opening of a stent and different lateral branch opening configurations are discussed in U.S. Pat. Nos. 6,210,429 and 6,325,826, co-pending U.S. Published Application Nos. 2004/0138737 and 2005/0015108, and co-pending U.S. patent application Ser. No. 10/644,550. Expanding the expandable structure surrounding the opening 52 can extend that expandable structure into the branch vessel 44 to treat, for example, the plaque 46a along carina 45.

After inflatable portions 28, 32 have been inflated to expand the stent 50, the inflation fluid filling the inflatable portions 28, 32 are drained via the inflation lumen 34. Draining the inflation fluid allows the inflatable portions 28 and 32 to collapse in preparation for withdrawal of the assembly 10 from vessel bifurcation 40.

After the inflatable portions 28, 32 are deflated and before withdrawal of the assembly 10, the distal end of the guidewire 36 can be repositioned within the main vessel 42 distally beyond the branch vessel 44. Repositioning of the guidewire 36 in the main vessel 42 before withdrawal of the system 10 may be useful if the guidewire 36 is used for additional treatment of the vessel bifurcation 40. One way to reposition the guidewire 36 is to proximally retract the guidewire and proximal portion 23 of the side catheter branch 20 out of the branch vessel 44 and lateral branch opening 52 of the stent 50. The guidewire 36 can then be advanced distally through the distal tip 39 directly into the main vessel 42. Alternatively, the guidewire 36 can be advanced distally through the distal tip 39, into the extension 21, through section 22a of the guidewire lumen 22, and out of the distal tip 19 of the main catheter branch 18.

In an alternative method of repositioning the guidewire 36 within the main vessel 42 after the stent is expanded as shown in FIG. 6, the guidewire 36 is retracted proximal of the proximal location P, and advanced distally through a second guidewire path or lumen. The second guidewire path includes, in addition to sections 22a and 22c, a section 22d that passes through the main lumen 29a of the main catheter branch 18 between locations P, D.

After the guidewire 36 is repositioned in the main catheter branch 18, the system 10 can be withdrawn proximally from the patient. In a further step, the guidewire 36 can also be withdrawn proximally from the patient.

III. The Example Illustrated in FIG. 7

FIG. 7 illustrates an alternative configuration for the distal end portion 16 of the bifurcation treatment system 10. A guidewire lumen 22 includes a first section 22a that extends within a proximal portion of main catheter shaft 12. A second section 22b of the guidewire lumen 22 extends through the side catheter branch 20. A side branch extension member 21 of the side catheter branch 20 includes an opening 25 along the length of the extension 21 between the gap G. The opening 25 is sized and arranged to permit the guidewire 36 to exit the assembly 10 along the second section 22b of the guidewire lumen 22. The opening 25 provides an exit path for the guidewire 36 without the guidewire being diverted back into the main vessel branch portion 18 at a location distal of location P.

The branch extension 21 can have openings at other locations along a length of the side catheter branch 20 for exit of the guidewire 36 other than the location of opening 25 shown in FIG. 7. Alternatively, the branch extension 21 can be completely removed. Removal of extension 21 does not preclude tracking the guidewire through the distal tip 39 of side catheter branch 20 and into the distal end of main catheter branch 18 distally of the expandable portions 28, 32. When the extension 21 is removed, the gap G can be defined adjacent to the distal location D. In still other examples, the extension 21 could be replaced with a fastener. The fastener can be configured to releaseably retain the distal end of guidewire 36. Alternatively, the fastener can be configured to releaseably retain the distal tip 39 of side catheter branch 20. Such a fastener could be positioned on, for example, the main catheter branch 18 distally of the expandable portions 28, 32. In another example, such a fastener could be positioned on one of the expandable portions 28, 32.

IV. Lumen Deformation Embodiments

With reference to FIGS. 8A-12B, several example arrangements illustrating the active movement of a side catheter branch 20 are shown and described. The active lifting away of the side catheter branch 20 can provide active seeking and location of the free end 39 of the side catheter branch 20 within the branch vessel 44. Further, the active lifting away of the side catheter branch 20 can provide increased torque transmission for alignment of the stent lateral branch opening 52 with the ostium of the branch vessel 44. Torque transmission can be an important consideration for maintaining alignment before and during expansion of the expandable members 28, 32.

There are a variety of ways to provide active movement of the side catheter branch 20. For example, the configuration of FIGS. 8A and 8B includes a side catheter branch 20 with potential energy stored therein. When the stored energy is released the side catheter branch 20 actively moves into an extended position. The potential energy can be generated, for example, by pre-forming the side catheter branch 20 into a shape such as the extended position shown in FIG. 8B. When the side catheter branch is bent into the retained position shown in FIG. 8B, potential energy is generated and stored in the side catheter branch. The extended configuration of side catheter branch 20 can also be generated by forming a particular cross-sectional shape in the side catheter branch 20 (e.g., see the cross-section of FIG. 10B) that can be inverted into a different cross-sectional shape (e.g., see the cross-section of FIG. 10A) to generate and store the potential energy.

Other methods of providing active movement of the side catheter branch are described with reference to FIGS. 11A-B. The side catheter branch can include a thermal shape memory material such as Nitinol (Nickel Titanium Naval Ordnance Laboratory) that provides bimodal actuation. Thermal shape memory material provides for a change in shape of the object that includes the material. The change in shape includes a change from a new shape into an original shape by heating the material above a transition temperature. The transition temperature for thermal shape memory materials such as Flexinol® made by Dynalloy of Costa Mesa, Calif., is about 70° C. The transition temperature of other thermal shape memory materials can be higher or lower depending on the specific material composition. When a thermal shape memory material is cooled, it can be stretched or otherwise formed into a new shape different from the original shape. By including thermal shape memory material in the side catheter branch 20 construction, the original shape can be the extended configuration of FIG. 11B and the shape maintained when below the transition temperature is the retained configuration of FIG. 11A.

Some types of thermal shape memory material can be heated to its transition temperature with the body heat of the patient into which the stent delivery system is introduced. Using the body as the heating source, it is possible to estimate a range of time required to reach the transition temperature beginning with introduction of the stent delivery system into the patient. Reducing the initial temperature of the side branch locator before introducing the side branch locator into the patient (e.g., by refrigerating portions of the bifurcation delivery system) can help extend the time period required for reaching the transition temperature after the side branch locator has been introduced into the patient. The thermal shape memory material can also be heated using an electric current or other heat source besides the patient's body.

Figure 11A:
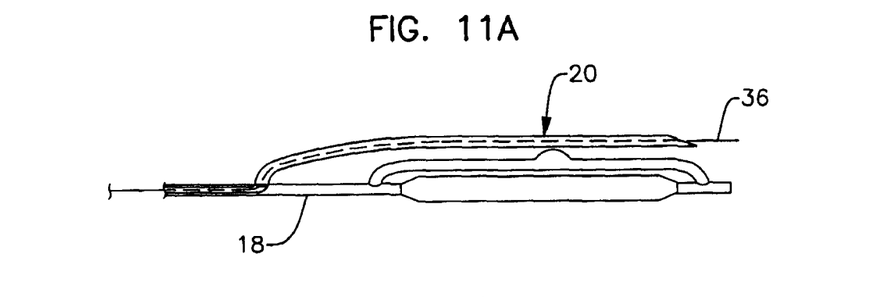
FIG. 11A is a schematic side view showing distal end features of an example bifurcation treatment system, wherein a position of the side catheter branch is controlled as a result of material properties of the side branch lumen.
Figure 11B:
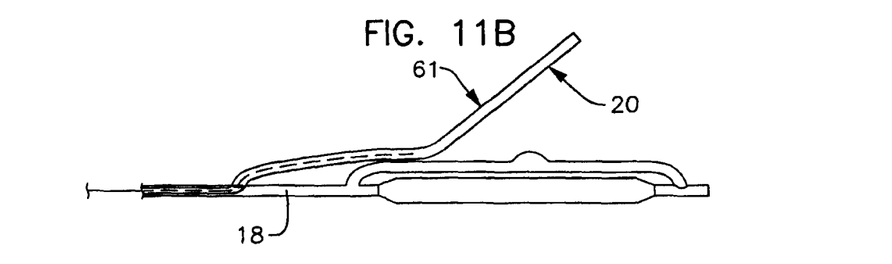
FIG. 11B is a schematic side view of the distal end features shown in FIG. 11A with the side catheter branch extending laterally from the main catheter branch.

Another example method of providing active movement of the side catheter branch 20 is to use current induced pseudo-elastic material in at least portions of the side catheter branch (e.g., in the bend section 61 shown in FIG. 11B). By administering a small current to the pseudo-elastic material, the material can be activated to move from the retained position of FIG. 11A to the extended position of FIG. 11B. A benefit of using pseudo elastic material in the side catheter branch 20 is that the side catheter branch can be changed from the extended position of FIG. 11B back to the retained position of FIG. 11A by altering the current applied to the material.

Figure 9A:
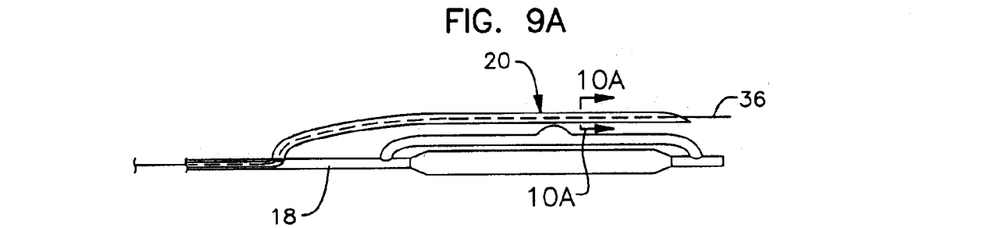
FIG. 9A is a schematic side view showing distal end features of another example bifurcation treatment system, wherein the side catheter branch is secured to the main catheter branch a result of the shape of the side catheter branch.
Figure 9B:
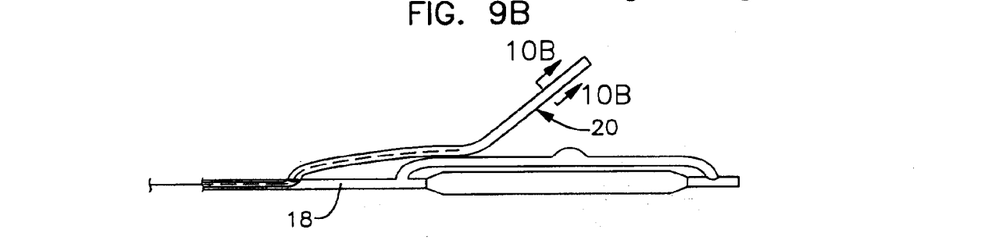
FIG. 9B is a schematic side view of the distal end features shown in FIG. 9A with the side branch lumen extending laterally from the main catheter branch upon release.
Figure 10A:
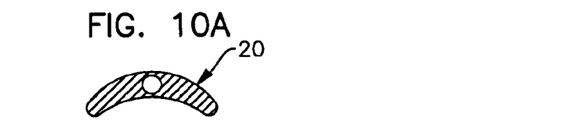
FIG. 10A is a schematic cross-sectional view of the side catheter branch shown in FIG. 9A taken along indicator 10A-10A.
Figure 10B:
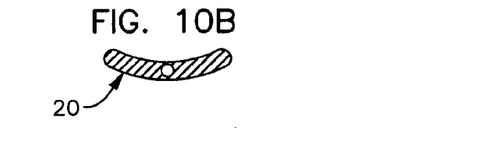
FIG. 10B is a schematic a cross-sectional view of the side catheter branch shown in FIG. 9A taken along indicator 10B-10B.

The side catheter branch 20 can be additionally held in the retained position of FIGS. 9A and 11A with a mechanical structure such as the retainer 60. Other features such as the inherent stiffness of the guidewire 36 passing through the side catheter branch 20 can be used to hold the side catheter branch in a retained position.

Figure 12A:
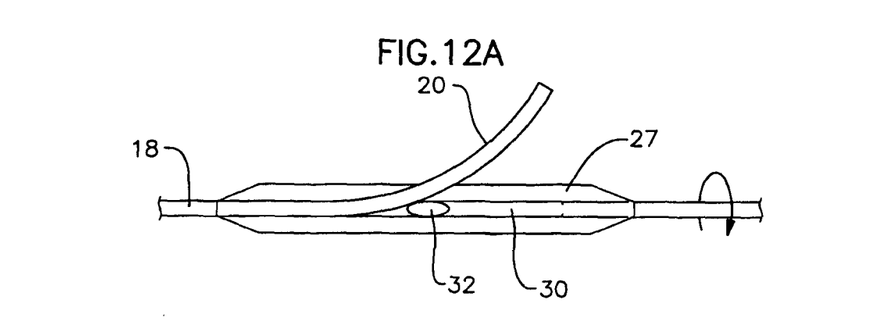
FIG. 12A is a schematic side view showing distal end features of an example bifurcation treatment system, wherein the side catheter branch extends in a first lateral direction.
Figure 12B:
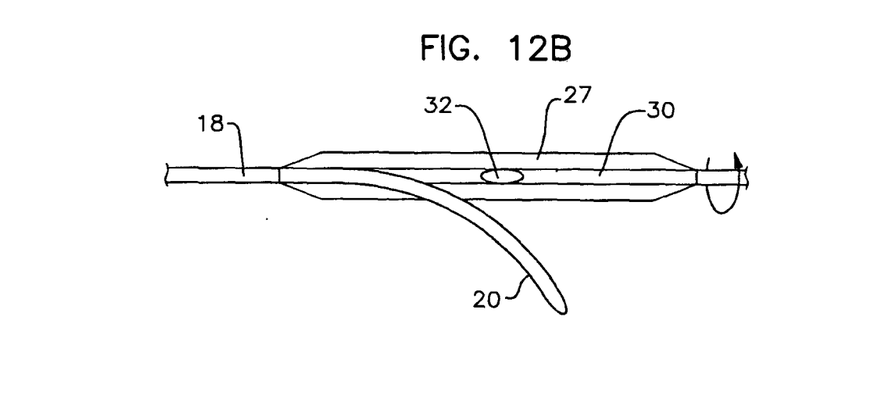
FIG. 12B is a schematic side view of the distal end features shown in FIG. 12A, wherein the side catheter branch extends in a second lateral direction.

The radial movement of side catheter branch 20 away from the main catheter branch 18 as shown in FIGS. 8A-B, 9A-B, and 11A-B can increase torque transmission. An increase in torque transmission can help achieve and maintain proper radial alignment of the bifurcation treatment system with the ostium of the branch vessel 44. Another way of providing torque transmission is to move the side catheter branch 20 in a lateral, side-to-side motion as shown in FIGS. 12A-B. Movement of the side catheter branch 20 in the right or left direction relative to the main catheter branch 18 (as shown in the top view of FIGS. 12A-B) can result in the desired radial rotational adjustment of the system 10 relative to the ostium of branch vessel 44. Advantages of the lateral movement of the side catheter branch 20 as shown in FIGS. 12A-B can be particularly effective if the distal end 39 of side catheter branch 20 is at least partially positioned within the branch vessel 44 while the main catheter branch 18 remains in the main vessel 42 of a vessel bifurcation 40.

V. Summary and Conclusion

One aspect of the present disclosure relates to a catheter assembly that includes a catheter shaft, a main catheter branch, a side catheter branch, and a first guidewire lumen. The catheter shaft has a distal end and defines a catheter shaft conduit. The main catheter branch has proximal and distal ends and defines a main catheter branch conduit. The main catheter branch extends from the distal end of the catheter shaft. The side catheter branch includes a distal guidewire receiver and a side catheter segment defining a side branch guidewire conduit. A distal end of the side catheter segment is spaced proximally from the distal guidewire receiver. The side catheter branch extends from the distal end of the catheter shaft at a proximal location with the side branch guidewire conduit in flow communication with the catheter shaft conduit. A proximal end of the side catheter branch is connected to the main catheter branch at a distal location with the distal guidewire receiver in flow communication with the main catheter branch conduit. The first guidewire lumen is defined by a portion of the catheter shaft conduit proximal of the proximal location and at least a portion of the side branch guidewire conduit distal of the proximal location.

Another aspect of the present disclosure relates to a method of positioning a catheter assembly relative to a vessel bifurcation. The catheter assembly includes a first guidewire lumen, a catheter shaft defining a catheter shaft conduit, a main catheter branch defining a main catheter branch conduit and extending from a distal end of the catheter shaft, and a side catheter branch including a distal guidewire receiver and a side catheter branch segment defining a side branch guidewire conduit. The distal guidewire receiver is spaced distally of the side catheter branch segment. The side catheter branch extends from catheter shaft at a proximal location with the side branch guidewire conduit in flow communication with the catheter shaft conduit. The side catheter branch is connected to the main catheter branch at a distal location. The first guidewire lumen is defined by a portion of the catheter branch conduit proximal of the proximal location and at least a portion of the side branch guidewire conduit. The method includes positioning a guidewire within a main vessel of the vessel bifurcation, inserting a proximal end of the guidewire into a distal end of the first guidewire lumen, and advancing the catheter assembly along the guidewire to the vessel bifurcation.

A still further aspect of the present disclosure relates to a catheter assembly that includes a catheter shaft, a main catheter branch, a side catheter branch, an inflatable balloon, a first guidewire lumen, and a stent. The catheter shaft defines a catheter shaft conduit. The main catheter branch defines a main catheter branch lumen and extends from a distal end of the catheter shaft. The inflatable balloon is positioned on the main catheter branch. The side catheter branch includes a distal guidewire receiver and a side catheter branch segment defining a side branch guidewire conduit. A distal end of the side catheter branch segment is spaced proximally from a proximal end of the distal guidewire receiver. The side catheter branch extends from the distal end of the catheter shaft at a proximal location proximal of a proximal end of the inflatable balloon. The side branch guidewire conduit is in flow communication with the catheter shaft conduit. The side catheter branch is connected to the main catheter branch at a distal location distal of a distal end of the inflatable balloon. The first guidewire lumen is defined by a portion of the catheter shaft conduit proximal of the proximal location, the side branch guidewire conduit, and a portion of the main catheter branch conduit distal of the distal location. The stent has a lateral branch opening and surrounds at least a portion of the inflatable balloon and at least a portion of the side catheter branch. The side catheter branch segment extends through the stent lateral branch opening.

It is noted that not all of the features characterized herein need to be incorporated within a given arrangement, for the arrangement to include improvements according to the present disclosure.

We claim:

1. A catheter assembly, comprising:
   a main catheter shaft including a proximal end and a distal end, the main catheter shaft defining a main guidewire lumen;
   an inflatable balloon disposed about a portion of the main catheter shaft;
   a side catheter branch including a proximal end and a distal end, the side catheter branch defining a side guidewire lumen, the proximal end of the side catheter branch coupled to and in fluid communication with the main catheter shaft at a location (P) proximal of the inflatable balloon and the distal end of the side catheter branch coupled to and in fluid communication with the main catheter shaft at a location (D) distal of the inflatable balloon, the side catheter branch including a proximal side catheter segment and a distal side catheter segment, a distal end of the proximal side catheter segment is separated by a gap from a proximal end of the distal side catheter segment, wherein the gap is material-free, wherein each of the proximal and distal side catheter segments are spaced radially from the balloon when inflated along their entire length by a branch balloon coupled to the main catheter shaft such that, when no guidewire is present in the side catheter branch, the proximal and distal side catheter segments are moveable relative to each other and relative to the balloon, wherein the side catheter branch does not include an inflatable balloon; and
   wherein the catheter assembly is adapted for use with only a single guidewire passing through the side guidewire lumen, the side guidewire lumen defined by a first portion of the main catheter shaft proximal of location (P), the proximal segment of the side catheter branch, the distal segment of the side catheter branch, and a second portion of the main catheter shaft distal of location (D);
   wherein the catheter assembly is configured such that when the single guidewire is withdrawn from the side guidewire lumen, into the main guidewire lumen proximal of location (P), the guidewire can then be advanced distally through the main guidewire lumen to a position distal of location (D).

2. The catheter assembly of claim 1, wherein a length of the side catheter branch between the proximal end and the distal end is at least 5% greater than a length of the main catheter shaft between the proximal end and the distal end of the side catheter branch.

3. The catheter assembly of claim 1, wherein the second portion of the main catheter shaft includes a sidewall and an aperture defined in the sidewall in flow communication with the distal end of the side catheter branch, the aperture sized to receive a guidewire therein.

4. The catheter assembly of claim 1, further comprising a stent extending around at least a portion of the inflatable balloon, at least a portion of the main catheter shaft, and at least a portion of the side catheter branch.

5. The catheter assembly of claim 4, wherein the stent includes a lateral branch opening, and the side catheter branch extends through the lateral branch opening.

6. The catheter assembly of claim 5, wherein the branch balloon is configured to extend radially away from the main catheter shaft when inflated, the branch balloon axially aligned with the stent lateral branch opening.

7. The catheter assembly of claim 5, wherein the distal side catheter segment is positioned radially outside of the stent and at least partially distal of the lateral branch opening.

8. The catheter assembly of claim 1, wherein a portion of the side catheter branch defines an arcuate shape.

9. A method of positioning a catheter assembly relative to a vessel bifurcation, the method comprising:
provingidng a catheter assembly including a main catheter shaft having a proximal end and a distal end and defining a main guidewire lumen, an inflatable balloon disposed about a portion of the main catheter shaft, a side catheter branch having a proximal end and a distal end and defining a side guidewire lumen, the proximal end of the side catheter branch coupled to the main catheter shaft at a location (P) proximal of the inflatable balloon and in fluid communication with a proximal portion of the main guidewire lumen of the main catheter shaft, the distal end of the side catheter branch coupled to the main catheter shaft at a location (D) distal of the inflatable balloon and in fluid communication with a distal portion of the main guidewire lumen of the main catheter shaft, the side catheter branch including a proximal side catheter segment separated from and moveable relative to a distal side catheter segment, the proximal and distal side catheter segments spaced radially from the balloon when inflated along their entire length by a branch balloon coupled to the main catheter shaft, the proximal side catheter segment biased away from the main catheter shaft, and a stent having a lateral branch opening, the stent surrounding at least a portion of the inflatable balloon and a portion of the proximal side catheter segment, a portion of the proximal side catheter segment extending through the stent lateral branch opening, the entire distal side catheter segment positioned outside of the stent distal of the stent lateral branch opening, wherein the side catheter branch does not include an inflatable balloon;
positioning a single guidewire within a main vessel of the vessel bifurcation;
inserting a proximal end of the guidewire into the distal portion of the main guidewire lumen of the main catheter shaft via an opening in the distal end of the main catheter shaft;
advancing the catheter assembly along the single guidewire to a position adjacent to the vessel bifurcation such that the proximal end of the guidewire passes through the distal portion of the main guidewire lumen of the main catheter shaft, the distal side catheter segment, the proximal side catheter segment, and the proximal portion of the main guidewire lumen of the main catheter shaft;
retracting a distal end of the single guidewire to a position proximal of the stent lateral branch opening, thereby allowing the portion of the proximal side catheter segment extending through the stent lateral branch opening to automatically move away from the main catheter shaft;
advancing the guidewire into an opening in a branch vessel of the vessel bifurcation;
advancing the catheter assembly over the guidewire such that a distal end of the proximal side catheter segment extends into the opening of the branch vessel;
repositioning the single guidewire into the main guidewire lumen by retracting a distal end of the guidewire proximally into the proximal portion of the main guidewire lumen, proximal of location (P), and then advancing the guidewire distally through just the main guidewire lumen toward location (D).

10. The method of claim 9, further comprising:
after advancing the catheter assembly such that the distal end of the proximal side catheter segment extends into the opening of the branch vessel, aligning the lateral branch opening of the stent with the branch vessel opening; and
expanding the stent to treat the vessel bifurcation.

11. A catheter assembly, comprising:
a main catheter shaft including a proximal end and a distal end, the main catheter shaft defining a main guidewire lumen;
an inflatable balloon positioned on the main catheter shaft;
a side catheter branch including a proximal end and a distal end, the side catheter branch defining a side guidewire lumen, the proximal end of the side catheter branch coupled to and in fluid communication with the main catheter shaft at a location (P) proximal of the inflatable balloon and the distal end of the side catheter branch coupled to and in fluid communication with the main catheter shaft at a location (D) distal of the inflatable balloon, the side catheter branch including a proximal side catheter segment and a distal side catheter segment, a distal end of the proximal side catheter segment is axially separated from and moveable relative to a proximal end of the distal side catheter segment, a distal end of the distal side catheter segment coupled to the main catheter shaft and the proximal end of the distal side catheter segment radially spaced from the main catheter shaft, the proximal and distal side catheter segments spaced radially from the balloon when inflated along their entire length by a branch balloon coupled to the main catheter shaft, wherein the side catheter branch does not include an inflatable balloon; and
a stent having a lateral branch opening, the stent surrounding at least a portion of the inflatable balloon and at least a portion of the proximal side catheter segment, the entire distal side catheter segment positioned outside of the stent distal of the stent lateral branch opening;
wherein the side guidewire lumen is defined by a first portion of the main catheter shaft proximal of location (P), the proximal segment of the side catheter branch, the distal segment of the side catheter branch, and a second portion of the main catheter shaft distal of location (D);
wherein the catheter assembly is configured for use with only a single guidewire, such that when the single guidewire is withdrawn from the side guidewire lumen, into the main guidewire lumen proximal of location (P), the guidewire can then be advanced distally through the main guidewire lumen to a position distal of location (D).

12. The catheter assembly of claim 11, wherein the distal side catheter segment is in flow communication with the main catheter shaft.

13. The catheter assembly of claim 11, further comprising a branch balloon coupled to the catheter shaft, the branch balloon configured to extend radially outwards when inflated relative to the main catheter branch, the branch balloon axially aligned with the stent lateral branch opening.

14. The catheter assembly of claim 11, wherein each of the proximal and distal side catheter segments are spaced radially from the inflatable balloon.

* * * * *